US00PP11600P

United States Patent [19]

Lemon

[11] Patent Number: Plant 11,600

[45] Date of Patent: Oct. 24, 2000

[54] VARIETY OF GERANIUM NAMED 'GLOBAL RUBY RED'

[75] Inventor: David G. Lemon, Lompoc, Calif.

[73] Assignee: Oglevee, Ltd., Connellsville, Pa.

[21] Appl. No.: 09/162,674

[22] Filed: Sep. 29, 1998

[51] Int. Cl.[7] ..... A01H 5/00

[52] U.S. Cl. ..... Plt./332

[58] Field of Search ..... Plt./332

[56] References Cited

U.S. PATENT DOCUMENTS

P.P. 7,271 7/1990 Guillou et al. ..... Plt./332

P.P. 8,885 9/1994 Klemm ..... Plt./332

*Primary Examiner*—Howard J. Locker
*Assistant Examiner*—Wendy Anne Baker
*Attorney, Agent, or Firm*—Webb Ziesenheim Logsdon Orkin & Hanson, P.C.

[57] ABSTRACT

The new variety of ivy geranium produces velvety flowers having a range of dark pink to bright ruby red to burgundy. The plant has high cutting yield, improved rooting time, controlled plant habit, but also has a neater floret presentation, improved heat tolerance and is less prone to oedema than other varieties in this market class.

1 Drawing Sheet

BACKGROUND OF THE INVENTION

This discovery relates to a new and distinct variety of *Pelargonium×peltatum* identified by the varietal name of 'Global Ruby Red' Breeder No. 4DG731 and Oglevee, Ltd. No. 5049. The seedling of the present variety was discovered in a selected breeding program in Connellsville, Pa. The new variety is a selection the crossing of the commercial variety 'Nicole', U.S. Plant Pat. No. 7,358, with an unpatented breeding variety (Oglevee, Ltd. No. 152). The new variety was first asexually reproduced on Jan. 23, 1995 at Oglevee, Ltd., 152 Oglevee Lane, Connellsville, Pa. 15425. It has been found to retain its distinctive characteristic through successive generations propagated by rooting tip cuttings in Connellsville, Pa. The new variety has been field trialed with outstanding success.

The new variety, when grown in a glass greenhouse in Connellsville, Pa. using full light, 60° F. night temperature, 68° F. day temperature and grown in a soilless media with constant fertilizer at 200–250 ppm nitrogen and potassium, has a response time of six weeks to flowering from a rooted cutting to flower in a 10 cm pot.

DESCRIPTION OF THE DRAWING

The accompanying photographic drawing illustrates the new variety, with the color being as nearly true as is possible with color illustrations of this type.

DESCRIPTION OF THE PLANT

The following detailed descriptions set forth the characteristics of the new variety. The data which define these characteristics were collected from asexual reproductions carried out at Oglevee, Ltd., 152 Oglevee Lane, Connellsville, Pa. 15425.

The color readings were taken indoors on Jun. 11, 1998 on a plant in a 20 cm pot in 200–220 foot candles of cool white fluorescent light. Color references are primarily to The R.H.S. Colour Chart of The Royal Horticultural Society of London.

THE PLANT

Classification:
- *Botanical.*—*Pelargonium×peltatum.*
- *Varietal.*—Ivy leafed Pelargonium named 'Global Ruby Red'.

Height: 13.0 cm from media.

Growth: Uniform, cascading mound suitable for a hanging basket.

Foliage: Stalked leaf attachment.

Rooting: Cuttings produce 3 to 5 roots visible to outside of artificial growing media in 14–21 days.

Leaves:
- *Size.*—6.0–7.5 cm across.
- *Shape.*—Reniform with cordate base.
- *Margin.*—Pedately lobed.
- *Texture.*—Leathery, pubescent.
- *Color.*—Top: Green Group 137A. Bottom: Green Group 137C. Zone: Yellow-Green Group 147A.
- *Ribs and veins.*—Venation: Palmate. Color: Yellow-Green Group 144A.

Petioles:
- *Length.*—3.5–6.0 cm.
- *Color.*—Yellow-Green Group 144A.

Stem:
- *Color.*—Yellow-Green Group 144A.
- *Internode length.*—4.0–6.0 cm.

THE BUD

Shape: Elongated.

Overall: Elliptical cluster when no color showing.

Individual buds: Elliptical or oval when no color showing.

Size: 3.0–4.0 cm across.

INFLORESCENCE

Blooming habit: Continuous blooming; double florets; 7–14 florets per umbel.

Borne: Umbel, florets on pedicel, pedicel on peduncle, 5.5–7.0 cm above foliage.

Closed florets:
- *Bud size.*—1.5 cm.

Open florets:
- *Form.*—Flat, ruffled.

*Size of fully open bloom.*—Umbels: 5.5–6.0 cm across. Florets: 2.5–3.5 cm across.

*Color.*—Top: Center is Red Group 53C blending to Red Group 53A at outer edge. Base of petal blends to Red Group 53D. Dark veining of Greyed-Purple Group 187A prominent on upper petals. Bottom: Speckling of Red Group 53D over white at center blending to Red Group 53A at edges.

*Eye.*—None.

*Petals.*—11–13 in number.

Texture and appearance: Velvety, smooth.

Tonality from a distance: Wide range of reds, including a dark pink, bright ruby red, and burgundy on these velvety flowers.

Petaloids:

*Quantity.*—2–3.

*Shape.*—Twisted irregular.

*Color.*—Top: Red Group 53C in center blending to Red Group 53A at outer edge. Bottom: Red Group 53D at center blending to Red Group 53A at edges.

Pedicel:

*Length.*—3.0–3.7 cm.

*Color.*—Yellow-Green Group 144A.

Peduncle:

*Length.*—10.0–12.0 cm.

*Color.*—Yellow-Green Group 144A.

Disease resistance: No unusual susceptibility to diseases of Pelargonium has been observed.

Lasting quality: Continuous blooming under outdoor conditions; new flower buds replace old very rapidly with blooms lasting 7–14 days and new umbels opening continuously; more heat tolerant and less susceptible to oedema than other varieties in this market class and does not turn yellow and drop foliage or stop blooming in July and August in Pennsylvania. as does Global Rich Red (U.S. Plant Pat. No. 10,443).

REPRODUCTIVE ORGANS

Stamens:

*Anthers.*—3.0 mm long.

*Filaments.*—9.0–11.0 mm long; white with pink tips.

*Pollen color.*—Golden orange.

Pistils:

*Number.*—1.

*Length.*—10.0–12.0 mm.

*Stigma.*—Dark red in color.

*Style.*—2.0–3.0 mm long.

*Ovaries.*—Pale green; 7.0 mm long.

Fruit: None observed.

GENERAL CHARACTERISTICS

The new variety brings a bright red to the "global" series. One clear difference between the new variety and it's parent variety, 'Nicole', is that it displays red blooms while 'Nicole' displays pale pink blooms. This variety also carries the other positive traits of the ivies in this group: high cutting yield, improved rooting time, controlled plant habit, but also has a neater floret presentation, improved heat tolerance and is less prone to oedemas.

I claim:

1. A New and distinct variety of geranium plant named 'Global Ruby Red' as described and illustrated herein.

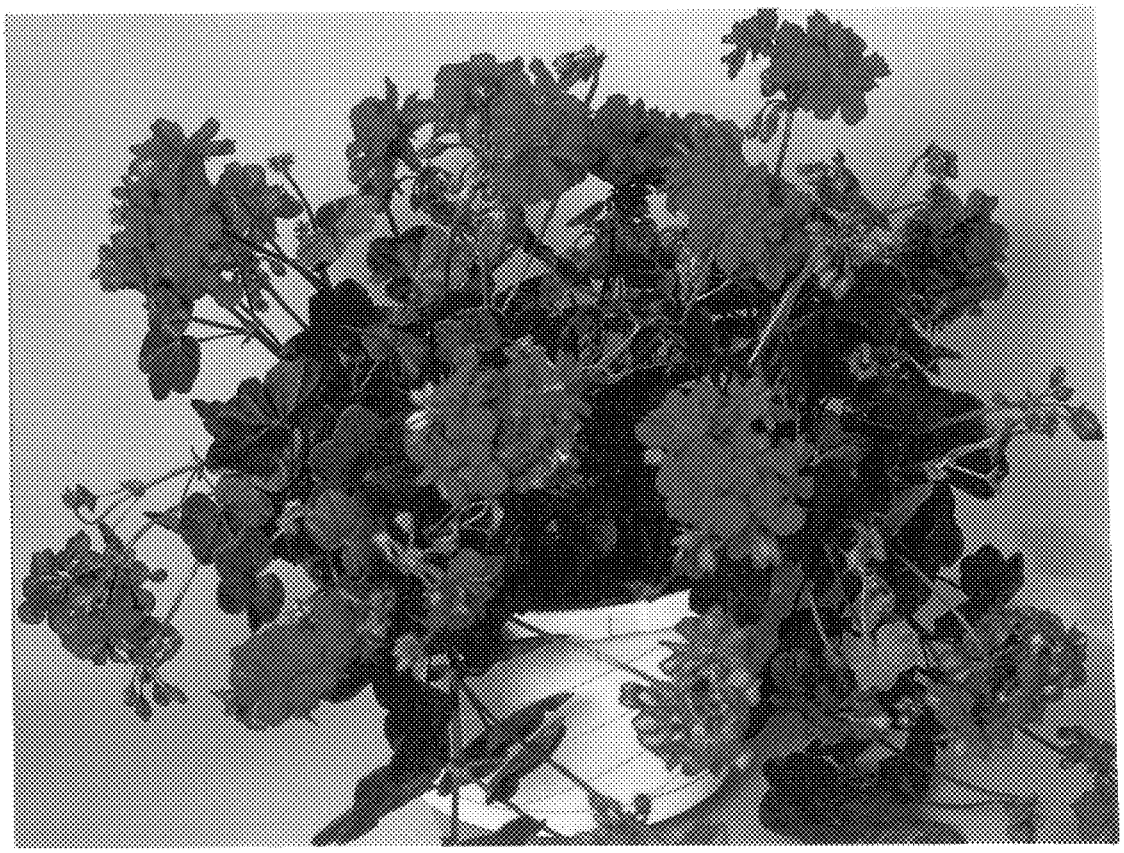

* * * * *